(12) United States Patent
Lamego et al.

(10) Patent No.: US 10,305,775 B2
(45) Date of Patent: *May 28, 2019

(54) PHYSIOLOGICAL TEST CREDIT METHOD

(71) Applicant: Cercacor Laboratories, Inc., Irvine, CA (US)

(72) Inventors: Marcelo M. Lamego, Coto De Caza, CA (US); Jeroen Poeze, Mission Viejo, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/713,275

(22) Filed: Sep. 22, 2017

(65) Prior Publication Data

US 2018/0069776 A1    Mar. 8, 2018

Related U.S. Application Data

(63) Continuation of application No. 14/071,447, filed on Nov. 4, 2013, now Pat. No. 9,787,568.

(60) Provisional application No. 61/722,245, filed on Nov. 5, 2012.

(51) Int. Cl.
| | |
|---|---|
| G06Q 20/08 | (2012.01) |
| H04L 12/26 | (2006.01) |
| G06Q 20/14 | (2012.01) |
| A61B 5/00 | (2006.01) |
| G06F 19/00 | (2018.01) |
| G06Q 50/22 | (2018.01) |
| A61B 5/1455 | (2006.01) |

(52) U.S. Cl.
CPC ............ *H04L 43/16* (2013.01); *A61B 5/0002* (2013.01); *G06F 19/00* (2013.01); *G06F 19/3418* (2013.01); *G06Q 20/145* (2013.01); *G06Q 50/22* (2013.01); *A61B 5/14551* (2013.01); *A61B 2560/028* (2013.01)

(58) Field of Classification Search
CPC ................... G06Q 20/08–20/18; G06Q 20/28
See application file for complete search history.

(56) References Cited

U.S. PATENT DOCUMENTS

| | | | |
|---|---|---|---|
| 4,960,128 | A | 10/1990 | Gordon et al. |
| 4,964,408 | A | 10/1990 | Hink et al. |
| 5,041,187 | A | 8/1991 | Hink et al. |
| 5,069,213 | A | 12/1991 | Polczynski |

(Continued)

OTHER PUBLICATIONS

US 8,845,543 B2, 09/2014, Diab et al. (withdrawn)
(Continued)

*Primary Examiner* — David R Lazaro
*Assistant Examiner* — Julian Chang
(74) *Attorney, Agent, or Firm* — Knobbe, Martens, Olson & Bear, LLP

(57) ABSTRACT

A physiological test credit method determines if test credits are available to the monitor and checks if a Wi-Fi connection is available. If test credits are less than a test credit threshold, the monitor connects to a test credit server, processes server commands so as to download test credits and disconnects from the server. In various embodiments, the monitor is challenged to break a server code, the server is challenged to break a monitor code. The server validates monitor serial codes, and saves monitor configuration parameters.

20 Claims, 7 Drawing Sheets

(56) References Cited

U.S. PATENT DOCUMENTS

| | | |
|---|---|---|
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,069,955 A * | 5/2000 | Coppersmith ....... G06Q 10/087 380/200 |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |

(56) References Cited

U.S. PATENT DOCUMENTS

| | | |
|---|---|---|
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,450,927 B1 * | 11/2008 | Creswell .............. H04L 12/14 455/405 |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |

(56) References Cited

U.S. PATENT DOCUMENTS

| | | |
|---|---|---|
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,725,645 B1* | 5/2014 | Montini ............... G06F 21/121 705/50 |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |

(56) References Cited

U.S. PATENT DOCUMENTS

| | | |
|---|---|---|
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,069,069 B2 * | 6/2015 | Freund .................... G01S 19/14 |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,787,568 B2 | 10/2017 | Lamego et al. |
| 2002/0138336 A1 * | 9/2002 | Bakes .................. G06Q 10/087 705/28 |
| 2002/0178126 A1 * | 11/2002 | Beck .................... A61B 5/0002 705/75 |
| 2003/0055794 A1 * | 3/2003 | Johnson ............ G07B 17/00435 705/403 |
| 2003/0063913 A1 * | 4/2003 | Yamazaki .............. G03G 15/55 399/8 |
| 2004/0068436 A1 * | 4/2004 | Boubek ................ G06Q 30/02 705/14.71 |
| 2004/0146328 A1 * | 7/2004 | Sasayama ................ G03F 7/30 400/118.2 |
| 2004/0236699 A1 * | 11/2004 | Beenau ............... G06K 9/00382 705/64 |
| 2004/0245330 A1 * | 12/2004 | Swift .................... G06Q 20/04 235/379 |
| 2004/0267552 A1 * | 12/2004 | Gilliam ................... G06F 21/10 705/59 |
| 2005/0125317 A1 * | 6/2005 | Winkelman, III ..... G06Q 20/04 705/30 |
| 2005/0247778 A1 * | 11/2005 | Roberts ................ G06Q 20/208 235/383 |
| 2006/0087407 A1 | 4/2006 | Stewart et al. |
| 2006/0149594 A1 * | 7/2006 | Hilligoss ................ G06Q 50/22 705/2 |
| 2006/0258917 A1 * | 11/2006 | Burd .................. A61B 5/14532 600/309 |
| 2006/0259328 A1 * | 11/2006 | Burd .................... A61B 5/0002 705/2 |
| 2007/0021843 A1 * | 1/2007 | Neill ...................... G06F 21/72 700/1 |
| 2007/0022015 A1 * | 1/2007 | Tarinelli ................ G06Q 10/02 705/5 |
| 2008/0089499 A1 * | 4/2008 | Hahn .................... H04M 15/00 379/114.2 |
| 2008/0097908 A1 * | 4/2008 | Dicks .................... A61B 5/0022 705/50 |
| 2008/0179401 A1 * | 7/2008 | Hart ...................... G06Q 20/341 235/449 |
| 2008/0251579 A1 * | 10/2008 | Larsen .................. G06Q 10/10 235/380 |
| 2009/0047926 A1 * | 2/2009 | Mastrantuono ........ G06Q 30/04 455/405 |
| 2009/0112769 A1 * | 4/2009 | Dicks .................... G06Q 50/22 705/51 |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0056875 A1 * | 3/2010 | Schoenberg .......... A61B 5/0002 600/300 |
| 2010/0145833 A1 | 6/2010 | Hamilton et al. |
| 2010/0204557 A1 * | 8/2010 | Kiaie .................. A61B 5/14532 600/365 |
| 2010/0268120 A1 * | 10/2010 | Eriksen ................ A61B 5/0806 600/587 |
| 2011/0073644 A1 * | 3/2011 | Sarkis, Jr. ............. G06Q 10/10 235/382 |
| 2011/0082711 A1 | 4/2011 | Poeze et al. |
| 2011/0105854 A1 | 5/2011 | Kiani et al. |
| 2011/0172498 A1 * | 7/2011 | Olsen ................ A61B 5/14551 600/300 |
| 2011/0179405 A1 * | 7/2011 | Dicks ....................... G06F 8/61 717/168 |
| 2011/0208015 A1 | 8/2011 | Welch et al. |

(56) References Cited

U.S. PATENT DOCUMENTS

| | | | |
|---|---|---|---|
| 2011/0208568 A1* | 8/2011 | Deitiker | G06Q 20/26 705/13 |
| 2011/0213212 A1 | 9/2011 | Al-Ali | |
| 2011/0230733 A1 | 9/2011 | Al-Ali | |
| 2011/0235792 A1* | 9/2011 | Foster | H04M 15/83 379/114.2 |
| 2011/0237911 A1 | 9/2011 | Lamego et al. | |
| 2012/0059267 A1 | 3/2012 | Lamego et al. | |
| 2012/0109685 A1* | 5/2012 | Carter | G06Q 50/22 705/3 |
| 2012/0143754 A1* | 6/2012 | Patel | G06Q 20/341 705/41 |
| 2012/0143772 A1* | 6/2012 | Abadir | G06Q 20/085 705/75 |
| 2012/0156337 A1* | 6/2012 | Studor | A47J 31/44 426/231 |
| 2012/0179006 A1 | 7/2012 | Jansen et al. | |
| 2012/0209082 A1 | 8/2012 | Al-Ali | |
| 2012/0209084 A1 | 8/2012 | Olsen et al. | |
| 2012/0283524 A1 | 11/2012 | Kiani et al. | |
| 2012/0296178 A1 | 11/2012 | Lamego et al. | |
| 2012/0319816 A1 | 12/2012 | Al-Ali | |
| 2012/0330112 A1 | 12/2012 | Lamego et al. | |
| 2013/0023775 A1 | 1/2013 | Lamego et al. | |
| 2013/0041591 A1 | 2/2013 | Lamego | |
| 2013/0046204 A1 | 2/2013 | Lamego et al. | |
| 2013/0060147 A1 | 3/2013 | Welch et al. | |
| 2013/0066644 A1* | 3/2013 | Dicks | A61B 5/0022 705/2 |
| 2013/0096405 A1 | 4/2013 | Garfio | |
| 2013/0096936 A1 | 4/2013 | Sampath et al. | |
| 2013/0097085 A1* | 4/2013 | Peckover | G06Q 30/018 705/50 |
| 2013/0117155 A1* | 5/2013 | Glasgo | G06Q 30/00 705/26.35 |
| 2013/0159456 A1* | 6/2013 | Daoud | H04L 67/12 709/217 |
| 2013/0160082 A1* | 6/2013 | Miller | H04L 63/08 726/3 |
| 2013/0190581 A1 | 7/2013 | Al-Ali et al. | |
| 2013/0211214 A1 | 8/2013 | Olsen | |
| 2013/0212381 A1* | 8/2013 | Bousamra | H04L 63/0823 713/156 |
| 2013/0243021 A1 | 9/2013 | Siskavich | |
| 2013/0246132 A1* | 9/2013 | Buie | G06Q 20/20 705/13 |
| 2013/0253334 A1 | 9/2013 | Al-Ali et al. | |
| 2013/0296672 A1 | 11/2013 | O'Neil et al. | |
| 2013/0312066 A1* | 11/2013 | Suarez | G06F 19/3418 726/4 |
| 2013/0317370 A1 | 11/2013 | Dalvi et al. | |
| 2013/0324808 A1 | 12/2013 | Al-Ali et al. | |
| 2013/0331670 A1 | 12/2013 | Kiani | |
| 2013/0338461 A1 | 12/2013 | Lamego et al. | |
| 2014/0012100 A1 | 1/2014 | Al-Ali et al. | |
| 2014/0034353 A1 | 2/2014 | Al-Ali et al. | |
| 2014/0037089 A1* | 2/2014 | Itoh | H04L 9/0869 380/46 |
| 2014/0051953 A1 | 2/2014 | Lamego et al. | |
| 2014/0066783 A1 | 3/2014 | Kiani et al. | |
| 2014/0077956 A1 | 3/2014 | Sampath et al. | |
| 2014/0081100 A1 | 3/2014 | Muhsin et al. | |
| 2014/0081175 A1 | 3/2014 | Telfort | |
| 2014/0094667 A1 | 4/2014 | Schurman et al. | |
| 2014/0100434 A1 | 4/2014 | Diab et al. | |
| 2014/0114199 A1 | 4/2014 | Lamego et al. | |
| 2014/0120564 A1 | 5/2014 | Workman et al. | |
| 2014/0121482 A1 | 5/2014 | Merritt et al. | |
| 2014/0121483 A1 | 5/2014 | Kiani | |
| 2014/0127137 A1 | 5/2014 | Bellott et al. | |
| 2014/0129702 A1* | 5/2014 | Lamego | A61B 5/0002 709/224 |
| 2014/0135588 A1 | 5/2014 | Al-Ali et al. | |
| 2014/0142401 A1 | 5/2014 | Al-Ali et al. | |
| 2014/0163344 A1 | 6/2014 | Al-Ali | |
| 2014/0163402 A1 | 6/2014 | Lamego et al. | |
| 2014/0166076 A1 | 6/2014 | Kiani et al. | |
| 2014/0171763 A1 | 6/2014 | Diab | |
| 2014/0180038 A1 | 6/2014 | Kiani | |
| 2014/0180154 A1 | 6/2014 | Sierra et al. | |
| 2014/0181524 A1* | 6/2014 | Itoh | H04L 9/3273 713/174 |
| 2014/0194766 A1 | 7/2014 | Al-Ali et al. | |
| 2014/0206963 A1 | 7/2014 | Al-Ali | |
| 2014/0213864 A1 | 7/2014 | Abdul-Hafiz et al. | |
| 2014/0243627 A1 | 8/2014 | Diab et al. | |
| 2014/0266790 A1 | 9/2014 | Al-Ali et al. | |
| 2014/0275808 A1 | 9/2014 | Poeze et al. | |
| 2014/0275835 A1 | 9/2014 | Lamego et al. | |
| 2014/0275871 A1 | 9/2014 | Lamego et al. | |
| 2014/0275872 A1 | 9/2014 | Merritt et al. | |
| 2014/0275881 A1 | 9/2014 | Lamego et al. | |
| 2014/0288400 A1 | 9/2014 | Diab et al. | |
| 2014/0303520 A1 | 10/2014 | Telfort et al. | |
| 2014/0316228 A1 | 10/2014 | Blank et al. | |
| 2014/0323825 A1 | 10/2014 | Al-Ali et al. | |
| 2014/0330092 A1 | 11/2014 | Al-Ali et al. | |
| 2014/0330098 A1 | 11/2014 | Merritt et al. | |
| 2014/0330099 A1 | 11/2014 | Al-Ali et al. | |
| 2014/0336481 A1 | 11/2014 | Shakespeare et al. | |
| 2014/0357966 A1 | 12/2014 | Al-Ali et al. | |
| 2015/0005600 A1 | 1/2015 | Blank et al. | |
| 2015/0011907 A1 | 1/2015 | Purdon et al. | |
| 2015/0012231 A1 | 1/2015 | Poeze et al. | |
| 2015/0018650 A1 | 1/2015 | Al-Ali et al. | |
| 2015/0025406 A1 | 1/2015 | Al-Ali | |
| 2015/0032029 A1 | 1/2015 | Al-Ali et al. | |
| 2015/0038859 A1 | 2/2015 | Dalvi et al. | |
| 2015/0045637 A1 | 2/2015 | Dalvi | |
| 2015/0048159 A1* | 2/2015 | Martinez de Velasco Cortina | G06Q 20/3227 235/379 |
| 2015/0051462 A1 | 2/2015 | Olsen | |
| 2015/0073925 A1* | 3/2015 | Renfroe | G06Q 30/0641 705/15 |
| 2015/0080754 A1 | 3/2015 | Purdon et al. | |
| 2015/0087936 A1 | 3/2015 | Al-Ali et al. | |
| 2015/0094546 A1 | 4/2015 | Al-Ali | |
| 2015/0097701 A1 | 4/2015 | Al-Ali et al. | |
| 2015/0099950 A1 | 4/2015 | Al-Ali et al. | |
| 2015/0099951 A1 | 4/2015 | Al-Ali et al. | |
| 2015/0099955 A1 | 4/2015 | Al-Ali et al. | |
| 2015/0101844 A1 | 4/2015 | Al-Ali et al. | |
| 2015/0106121 A1 | 4/2015 | Muhsin et al. | |
| 2015/0112151 A1 | 4/2015 | Muhsin et al. | |
| 2015/0116076 A1 | 4/2015 | Al-Ali et al. | |
| 2015/0126830 A1 | 5/2015 | Schurman et al. | |
| 2015/0133755 A1 | 5/2015 | Smith et al. | |
| 2015/0141781 A1 | 5/2015 | Weber et al. | |
| 2015/0165312 A1 | 6/2015 | Kiani | |
| 2015/0196237 A1 | 7/2015 | Lamego | |
| 2015/0201874 A1 | 7/2015 | Diab | |
| 2015/0207626 A1* | 7/2015 | Neftel | G08C 17/02 713/168 |
| 2015/0216459 A1 | 8/2015 | Al-Ali et al. | |
| 2015/0230755 A1 | 8/2015 | Al-Ali et al. | |
| 2015/0238722 A1 | 8/2015 | Al-Ali | |
| 2015/0245773 A1 | 9/2015 | Lamego et al. | |
| 2015/0245794 A1 | 9/2015 | Al-Ali | |
| 2015/0257689 A1 | 9/2015 | Al-Ali et al. | |
| 2015/0272514 A1 | 10/2015 | Kiani et al. | |
| 2015/0351697 A1 | 12/2015 | Weber et al. | |
| 2015/0351704 A1 | 12/2015 | Kiani et al. | |
| 2015/0359429 A1 | 12/2015 | Al-Ali et al. | |
| 2015/0366472 A1 | 12/2015 | Kiani | |
| 2015/0366507 A1 | 12/2015 | Blank | |
| 2015/0374298 A1 | 12/2015 | Al-Ali et al. | |
| 2015/0380875 A1 | 12/2015 | Coverston et al. | |
| 2016/0000362 A1 | 1/2016 | Diab et al. | |
| 2016/0007930 A1 | 1/2016 | Weber et al. | |
| 2016/0029932 A1 | 2/2016 | Al-Ali | |
| 2016/0045118 A1 | 2/2016 | Kiani | |

(56) References Cited

U.S. PATENT DOCUMENTS

| | | |
|---|---|---|
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Kind et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014084 A1 | 1/2017 | Al-Ali et al. |
| 2017/0021099 A1 | 1/2017 | Al-Ali et al. |
| 2017/0027456 A1 | 2/2017 | Kinast et al. |
| 2017/0042488 A1 | 2/2017 | Muhsin |
| 2017/0055847 A1 | 3/2017 | Kiani et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |

OTHER PUBLICATIONS

US 9,579,050 B2, 02/2017, Al-Ali (withdrawn)
"E-ZPass Quick Guide," https://web.archive.org/web/20121217041418/https://www.e-zpassny.com/en/about/i_guide.pdf, archived Jan. 6, 2012.
"E-ZPass User's Manual," https://web.archive.org/web/20120417132149/http://www.paturnpike.com/ezpass/pdf/EZPass_User_Manual.pdf, archived on Apr. 17, 2012.

* cited by examiner

PHYSIOLOGICAL TEST CREDIT METHOD

PRIORITY CLAIM AND REFERENCE TO RELATED APPLICATIONS

The present application is a continuation of U.S. patent application Ser. No. 14/071,447, filed Nov. 4, 2013, now U.S. Pat. No. 9,787,568, titled Physiological Test Credit Method, claims priority benefit under 35 U.S.C. § 119(e) to U.S. Provisional Patent Application Ser. No. 61/722,245, filed Nov. 5, 2012, titled Physiological Test Credit System, hereby incorporated in its entirety by reference herein.

BACKGROUND OF THE INVENTION

Pulse oximetry is a widely accepted noninvasive procedure for measuring the oxygen saturation level of arterial blood, an indicator of a person's oxygen supply. A typical pulse oximetry system utilizes a sensor applied to a patient tissue site. The sensor has emitters that transmit optical radiation having red and infrared (IR) wavelengths into the tissue site. A detector responds to the intensity of the optical radiation after attenuation by pulsatile arterial blood flowing within the tissue site. Based on this response, a processor determines measurements for oxygen saturation and pulse rate. In addition, a pulse oximeter may display a plethysmograph waveform, which is a visualization of blood volume change within the illuminated tissue caused by the pulsatile arterial blood flow over time.

Pulse oximeters capable of reading through motion induced noise are available from Masimo Corporation ("Masimo") Irvine, Calif. Moreover, portable and other pulse oximeters capable of reading through motion induced noise are disclosed in at least U.S. Pat. Nos. 6,770,028, 6,658,276, 6,157,850, 6,002,952 5,769,785, and 5,758,644, which are all assigned to Masimo and are all incorporated in their entireties by reference herein. Corresponding low noise sensors are also available from Masimo and are disclosed in at least U.S. Pat. Nos. 6,985,764, 6,813,511, 6,792,300, 6,256,523, 6,088,607, 5,782,757 and 5,638,818, which are all assigned to Masimo and are all incorporated in their entireties by reference herein. Such reading through motion pulse oximeters and low noise sensors have gained rapid acceptance in a wide variety of medical applications, including surgical wards, intensive care and neonatal units, general wards, home care, physical training, and virtually all types of monitoring scenarios.

Noninvasive blood parameter monitors capable of measuring blood parameters in addition to $SpO_2$, such as HbCO, HbMet and total hemoglobin (Hbt) and corresponding multiple wavelength optical sensors are also available from Masimo. Noninvasive blood parameter monitors and corresponding multiple wavelength optical sensors are described in at least U.S. patent application Ser. No. 11/367,013, filed Mar. 1, 2006 and entitled Multiple Wavelength Sensor Emitters and U.S. patent application Ser. No. 11/366,208, filed Mar. 1, 2006 and entitled Noninvasive Multi-Parameter Patient Monitor, both assigned to Cercacor Laboratories, Inc. ("Cercacor") Irvine, Calif. and both incorporated in their entireties by reference herein.

Further, physiological monitoring systems that include low noise optical sensors and pulse oximetry monitors, such as any of LNOP® adhesive or reusable sensors, SofTouch™ sensors, Hi-Fi Trauma™ or Blue™ sensors; and any of Radical®, SatShare™, Rad-9™, Rad-5™, Rad-5V™ or PPO+™ Masimo SET® pulse oximeters, are all available from Masimo. Physiological monitoring systems including multiple wavelength sensors and corresponding noninvasive blood parameter monitors, such as Rainbow™ adhesive and reusable sensors and RAD-57™ and Radical-7™ monitors for measuring $SpO_2$, pulse rate, perfusion index, signal quality, HbCO and HbMet among other parameters are also available from Masimo.

SUMMARY OF THE INVENTION

A physiological monitoring system has a sensor that transmits optical radiation at a multiplicity of wavelengths and a monitor that determines the relative concentrations of blood constituents such as $HbO_2$, Hb, carboxyhemoglobin (HbCO), methemoglobin (MetHb), fractional oxygen saturation, total hemoglobin (Hbt) and blood glucose to name a few. The monitor advantageously utilizes test credits each of which represent a quantum of currency. A test credit enables the monitor to make a physiological measurement. In various embodiments different monitor buttons are pressed to measure different variables. For example, one button initiates a $SpO_2$ measurement and another button initiates a SpCO measurement. After the measurement, the number of available test credits are decremented. The sensor has a memory that stores the test credits, which is decremented after each test. The monitor reads the sensor memory so as to determine the remaining test credits. Physiological monitoring systems include a Masimo Pronto-7® and corresponding rainbow 4D™ DC sensor. The Pronto-7 is a palm-sized device designed for quick-and-easy noninvasive total hemoglobin (SpHb®) spot-check testing, along with $SpO_2$, pulse rate, and perfusion index. A spot check monitor and corresponding credit system is described in U.S. patent application Ser. No. 12/882,111 titled Spot Check Monitor Credit System, filed Sep. 14, 2010 and U.S. patent application Ser. No. 13/110,833 titled Spot Check Monitor Credit System, filed May 18, 2011, both assigned to Cercacor and both incorporated in their entireties by reference herein.

An aspect of a physiological test credit method programmatically initiates wireless communications between a physiological monitor and a remote server in response to available test credits falling below a predetermined threshold so as to download additional test credits from the server to the monitor and therefore enable the monitor to perform additional physiological parameter spot-checks on a per test credit basis. The physiological test credit system establishes a threshold for test credits stored in an optical sensor attached to a corresponding physiological monitor. A server is securely connected to the monitor when remaining test credits fall below the threshold, and test credits are downloaded from the server to the monitor accordingly. In various embodiments, a quantum of test credits is defined and an amount of test credits equal to the quantum is downloaded each time the remaining test credits fall below the threshold. A download frequency is defined according to the number of times remaining test credits fall below the threshold in a given period of time. The threshold is adjusted according to the download frequency. Alternatively, or in addition to adjusting the threshold, the quantum is adjusted according to the download frequency.

In various other embodiments, challenges are exchanged between the server and the monitor so as to verify both the server and the monitor. The challenges may include sending a server challenge code to the monitor and breaking the server challenge code with the monitor and sending a monitor challenge code to the server and breaking the monitor challenge code with the server. The monitor may be validated utilizing sales data. Also, the server may send a request for device serial numbers to the monitor, and the serial numbers are matched to sales data. Further, monitor validation may include sending a server request for a zip code to the monitor and matching the zip code to the monitor account.

Another aspect a physiological test credit method is determining a test credit quantity associated with a physiological sensor, comparing the test credit quantity to a threshold and wirelessly connecting a physiological monitor to a server if the test credit quantity is below the threshold. Server commands are processed so as to download additional test credits to the monitor. Additional test credits are transferred to the physiological sensor, and the physiological monitor is disconnected from the server.

In various embodiments, the frequency of test credit downloads are tracked and, at least periodically, the amount of additional test credits downloaded are adjusted according to the frequency. The threshold may be adjusted, at least periodically, according to the frequency. The monitor may be challenged to break a server code before any test credits are downloaded to the monitor. The server may be challenged to break a monitor code before any test credits are downloaded to the monitor.

A further aspect of a physiological test credit method comprises establishing a wireless connection between a monitor and a server; downloading a file of test credits from the server to the monitor; transferring the test credits to a sensor in communications with the monitor; performing a physiological test on a person using the sensor; displaying a result of the physiological test on the monitor; deducting a test credit from the sensor in response to the test; and downloading an additional file of test credits from the server to the monitor in response to the number of test credits remaining in the sensor falling below a threshold.

In various embodiments, a quantity of test credits contained in the additional file are defined and adjusted according to the time between the downloading of the file and the downloading of the additional file. The threshold is adjusted according to the time between the downloading of the file and the downloading of the additional file. A two-way challenge is performed between the monitor and the server before downloading a file of test credits. The two-way challenge comprises sending a server challenge code to the monitor; breaking the server challenge code at the monitor; sending a monitor challenge code to the server; and breaking the monitor challenge code at the server. The sensor and the monitor serial numbers are sent to the server, and the serial numbers are matched with sales data available to the server. Monitor configuration parameters are saved on the server.

Yet another aspect of a physiological test credit system establishes wireless communications between a physiological monitor and a remote server. The server downloads test credits from the server to a sensor attached to the monitor. Each test credit allows the monitor to perform a spot-check of a physiological parameter. The monitor initiates a test credit download when the number of available test credits for a sensor falls below a test credit threshold. The monitor establishes a wireless connection with a server. The monitor and server perform a two-way challenge so that each can verify a connection to an approved device. The server also authenticates the monitor's account on the server. If the challenges and authentication are successful, the server downloads a credit file of test credits to the monitor and its attached sensor. The monitor and server then disconnect.

An additional aspect of a physiological test credit method establishes wireless communications between a physiological monitor and a remote server so as to download test credits to the monitor and its attached optical sensor. This enables the monitor to perform physiological parameter spot-checks on a per test credit basis. The physiological test credit method establishes a minimum threshold for test credits stored in an optical sensor attached to a corresponding physiological monitor and connects a server to the monitor when remaining test credits fall below the minimum threshold. The server-monitor connection first requires the monitor and server to exchange mutual code-breaking challenges for server-monitor verification. The server is then allowed to authenticate the monitor user account and funds. The server further validates the monitor via sales data. Monitor settings are saved to the server, and server commands are sent to the monitor.

In various embodiments, a server command is sent to the monitor to download configuration parameters including the test credit minimum threshold. The first time a monitor is connected to a server, a one-time monitor setup is performed. In exchanging challenges a server challenge code is sent to the monitor. The monitor must break the server challenge code. Then the monitor sends a challenge code to the server, which the server must break. Monitor validation involves a server request for device serial numbers from the monitor, which are matched with sales data. The server also requests a monitor zip code, which is matched with the monitor account. In various other embodiments, user settings are saved in the monitor and downloaded to the server. The server sends monitor commands that comprise OP commands to perform a monitor functions, GUI commands to display results and hybrid command to initiate a user response.

A further aspect of a physiological test credit method comprises establishing a wireless connection between a monitor and a server, performing a two-way challenge between the monitor and the server, authenticating the monitor and validating the monitor. The method may further comprise transferring a credit file of test credits from the server to the monitor, performing a physiological test, deducting a test credit corresponding to the test from the monitor account, and disconnecting the monitor and the server. The server also performs a one-time monitor setup.

In various embodiments, the two-way challenge includes sending a first challenge code from the server to the monitor, breaking the first challenge code at the monitor, sending a second challenge code from the monitor to the server and breaking the second challenge code at the server. A monitor validation comprises sending sensor and monitor serial numbers to the server, matching the serial numbers with sales data available to the server, sending a zip code to the server and matching the zip code with account information available to the server. Authenticating may comprise verifying the monitor's user account and funds. Setting-up the monitor may comprise sending commands and queries to the monitor so as to receive configuration parameters.

Another aspect of a physiological test credit method determines if test credits are available to the monitor and checks if a Wi-Fi connection is available. If test credits are less than a test credit threshold, the monitor connects to a test credit server, processes server commands so as to download test credits and disconnects from the server. In various embodiments, the monitor is challenged to break a server code, the server is challenged to break a monitor code. The server validates monitor serial codes, and saves monitor configuration parameters.

DETAILED DESCRIPTION OF THE PREFERRED EMBODIMENTS

Figure 1:
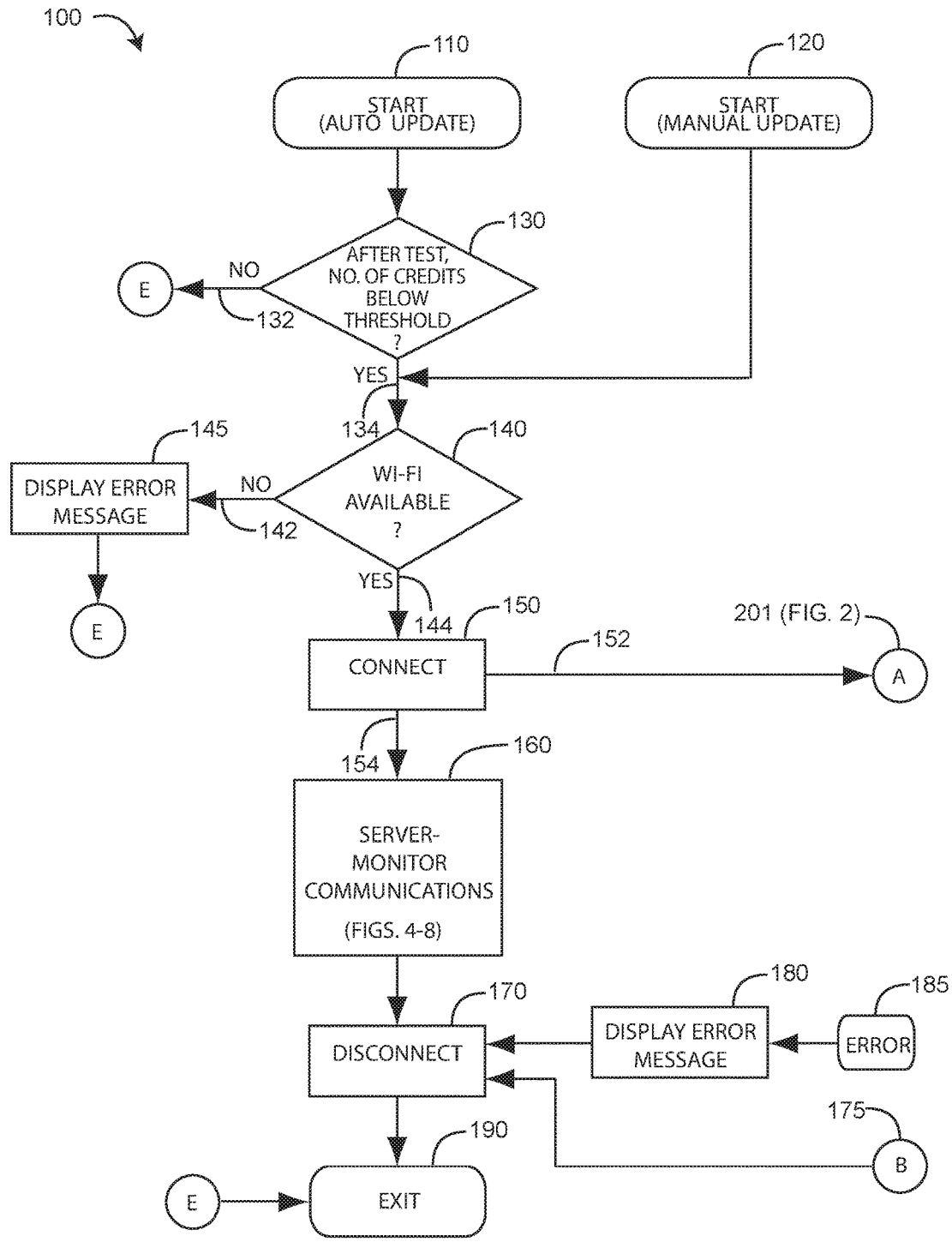
FIG. 1 is a flowchart of a monitor-side physiological test credit method.
Figure 2:
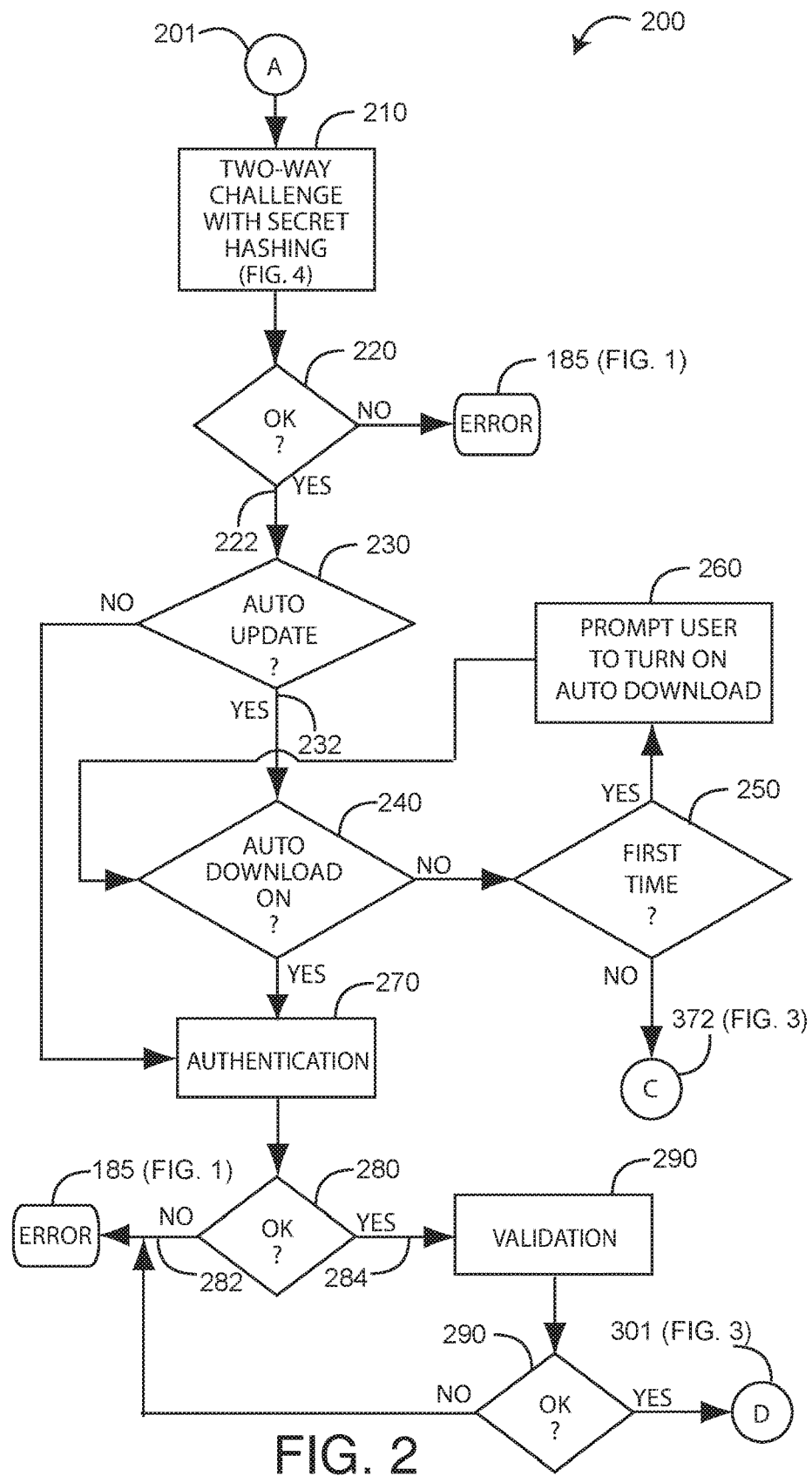
FIGS. 2-3 are flowcharts of a server-side physiological test credit method.
Figure 3:
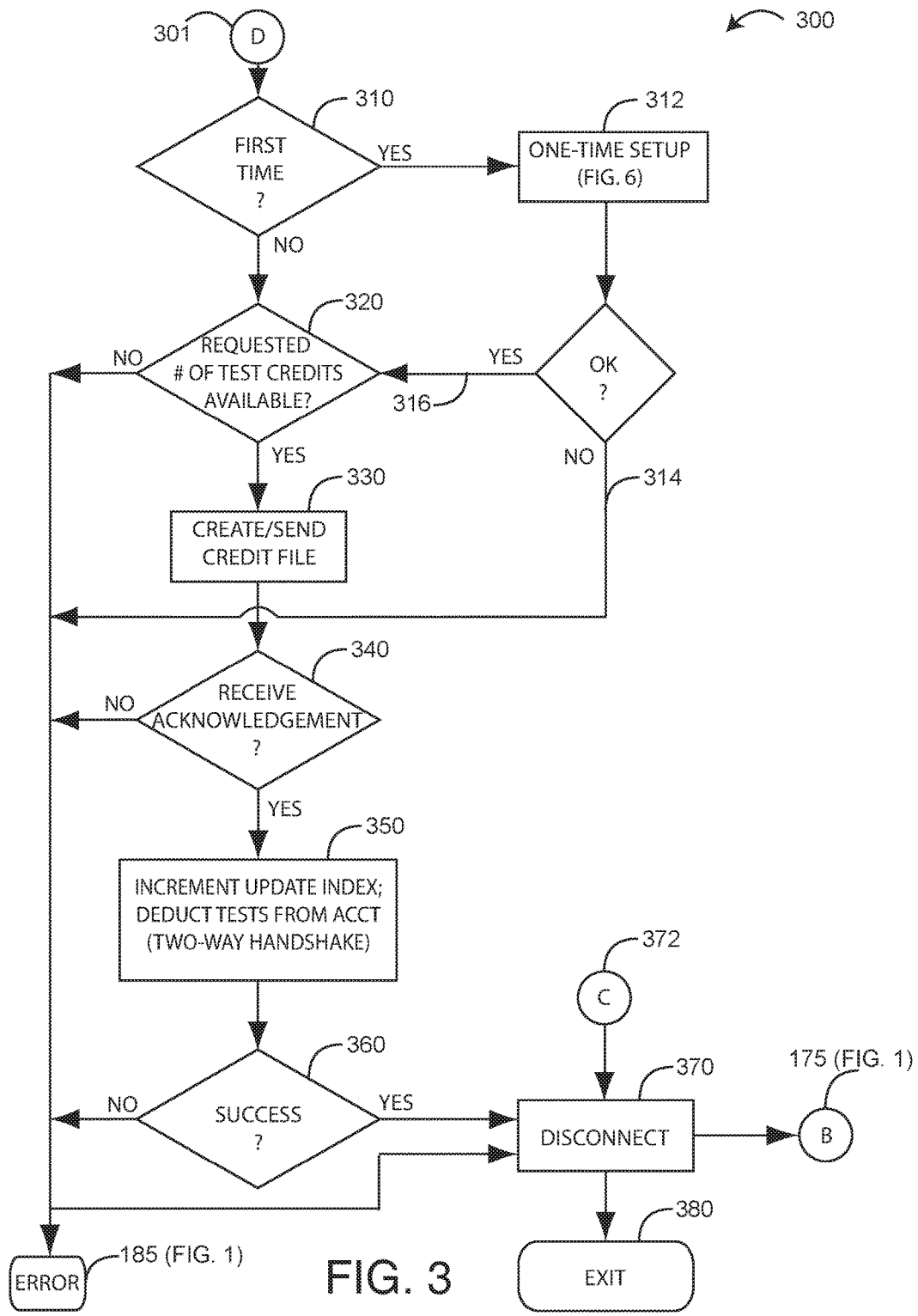

FIGS. 1-3 illustrate test credit downloads to a monitoring device using a broadband connection, such as Wi-Fi. In an embodiment, the monitor always initiates the connection. There are two ways a user can download test credits. "Automatic download" or "Manual download." For automatic downloads, the monitor initiates the connection after a test is performed and the available test credits fall below a predefined update threshold. For manual downloads, a user initiates the connection using a monitor menu flow. Accordingly, when a monitor initiates a connection, the initial connection request will have a parameter that describes whether or not a user manually initiated the connection.

For an automatic download, the monitor initiates a connection to a test credit server after a test is performed and the test credits drop below a user-predefined update threshold. In an embodiment, a user-predefined quantum of test credits (an integer between 1 and N inclusive) is downloaded each time the update threshold is crossed. In an embodiment, the test credit update threshold and the test credit download quantum are user-defined. In an embodiment, the monitor automatically adjusts the test credit download quantum and/or the test credit update threshold according to the frequency of test credit usage so as to advantageously reduce the frequency of server connections during periods of heavy monitor usage and to advantageously spread-out test credit expenditures during periods of light monitor usage. In an embodiment, the relationship between test credit download quantum, test credit update threshold and test credit usage is user defined.

The process of updating the test credits is done in the background. However, a user will not be able to perform a test during this period. If insufficient test credits are available for auto-download, a server may query/inform a user about this scenario via GUI commands to the monitor. A monitor initiates a manual download via a local GUI. Then the server takes over the process as with an auto download mode.

FIG. 1 illustrates a test credit download process from a monitor perspective 100. A monitor test credit download can be initiated automatically 110. After a test is complete, the number of available tests credits on a connected sensor is determined and compared with a specified update threshold 130. If the available test credits have not fallen below that threshold 132, the update process exits 190. If the number of test credits are below that threshold 134, the update process continues.

Also shown in FIG. 1, alternatively, a monitor test credit download can be initiated manually when a user selects a manual test credit update menu option 120. For either auto update 110 or manual update 120, Wi-Fi availability is determined 140. If there is no Wi-Fi 142, the process displays an error message 145 and exits 190. If Wi-Fi is available 144, a connection 150 to a server is attempted 152, as described below. Once a server connection is established 154, the monitor processes commands from the server 160, disconnects 170 and exits 190.

FIGS. 2-3 illustrate a test credit download process from a server perspective. As shown in FIG. 2, immediately after a Wi-Fi connection is established between monitor and server, the server initiates a two-way challenge with secret hashing 210. Both the server and the monitor use a two-way challenge to verify their connection with a real monitor or server, respectively, as described in detail with respect to FIG. 4, below. If the challenge 210 is successful 222, the server determines if the update is manual or automatic 230. If automatic 232, the server verifies that the user has turned on the auto download feature 240, prompting the user 250, 260 if necessary. If the auto download remains off, the server disconnects 372 (FIG. 3). With either the manual or automatic update, a secure authentication 270 is performed, which verifies the user's account and funds. If authentication fails 282, an error 185 (FIG. 1) is returned to the monitor, an error message is displayed 180 (FIG. 1) and the monitor disconnects 170 (FIG. 1). If authentication succeeds 284, validation is performed 301 (FIG. 3).

As shown in FIG. 2, once the user's account is authenticated, the customer and/or monitor and sensor are validated 290. In part, this step insures that customers, monitors and sensors are paired to the appropriate manufacturer or distributor. This can be a one-time validation or a validation for every credit download.

As shown in FIG. 3, when the server recognizes that a monitor is connecting for the first time 310, the server performs a one-time setup 312, as described with respect to FIG. 6, below. If there is any problems with the setup 314, the server sends an error 185 (FIG. 1) to the monitor, drops the connection 370 and exits 380. If the setup 312 is currently successful 316 or was previously performed 310, the server determines if the requested number of test credits are available 320. If so, the credit file is created and sent to the monitor 330. If not, an error is returned to the monitor 185 (FIG. 1), and the server disconnects 370 and exits 380.

Further shown in FIG. 3, after the monitor receives a credit file from the server 330. The monitor sends an ACK and the server receives the ACK 340. Using hand-shaking, either zero or all three of the following operations take place: the server deducts the credit from user account; the server increments the index count; and/or the monitor updates credits into the sensor 350.

Additionally shown in FIG. 3, the server drops the connection 370 upon successful completion of the process 360 or if it recognizes any error 185 (FIG. 1). The monitor drops the connection 170 (FIG. 1) if the server does not meet the monitor's challenge or the monitor recognizes an error 185 due to any reason.

Figure 4:
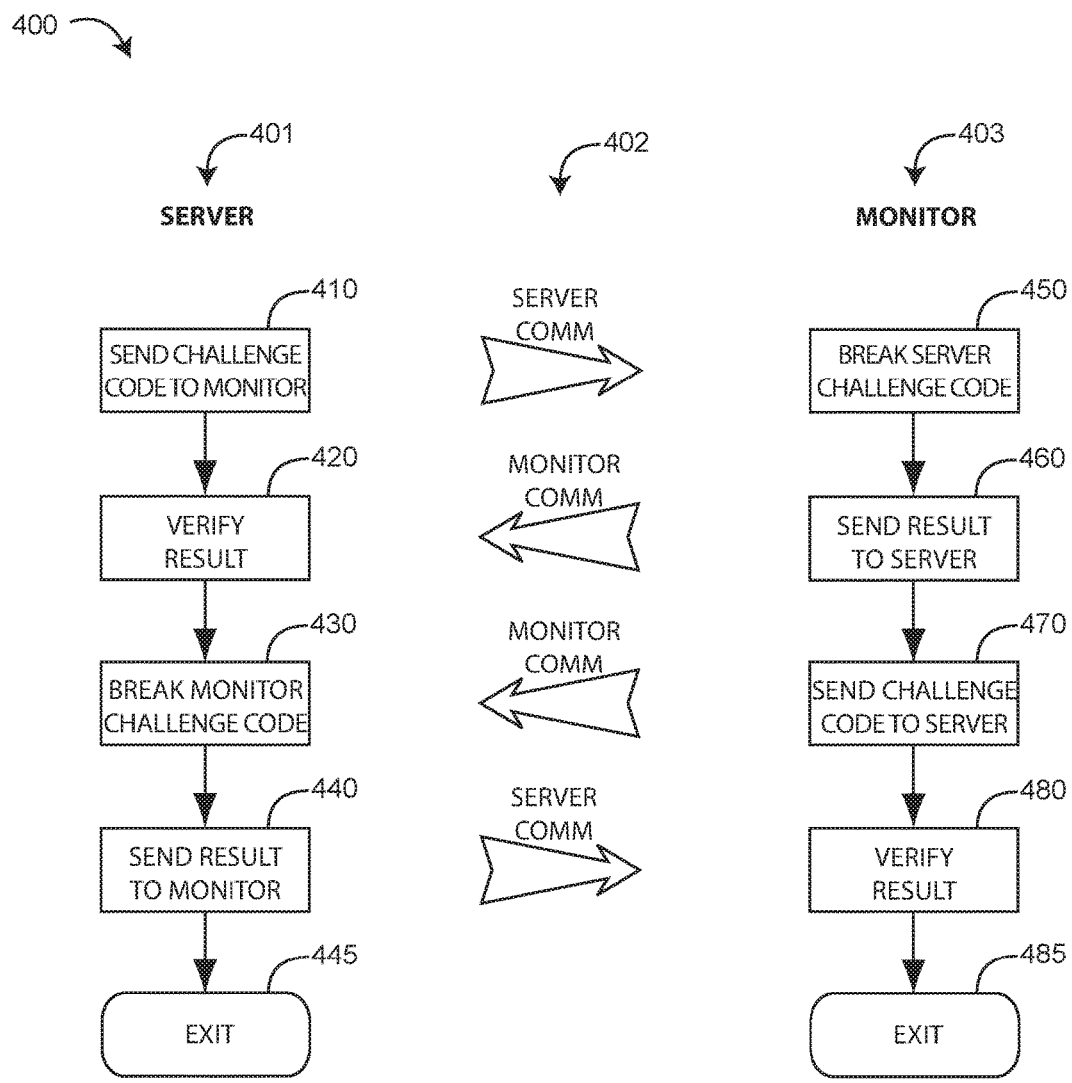
FIG. 4 is a flowchart of a two-way challenge for both the server and the monitor to verify their connections.

FIG. 4 illustrates the two-way challenge 400 for both the server 401 and the monitor 403 to verify their connections. In order to do that, both the monitor and the server challenge each other with a code to break, which only a real server and a real monitor know how to do. In particular, the server 410 first challenges the monitor 450 to break a code. If the server sees that the device cannot break the code 420, the server drops the connection. Otherwise, the server 430 asks the monitor 470 to send the server a code to break. If the monitor sees that the server cannot break the code 480, the monitor drops the connection.

Figure 5:
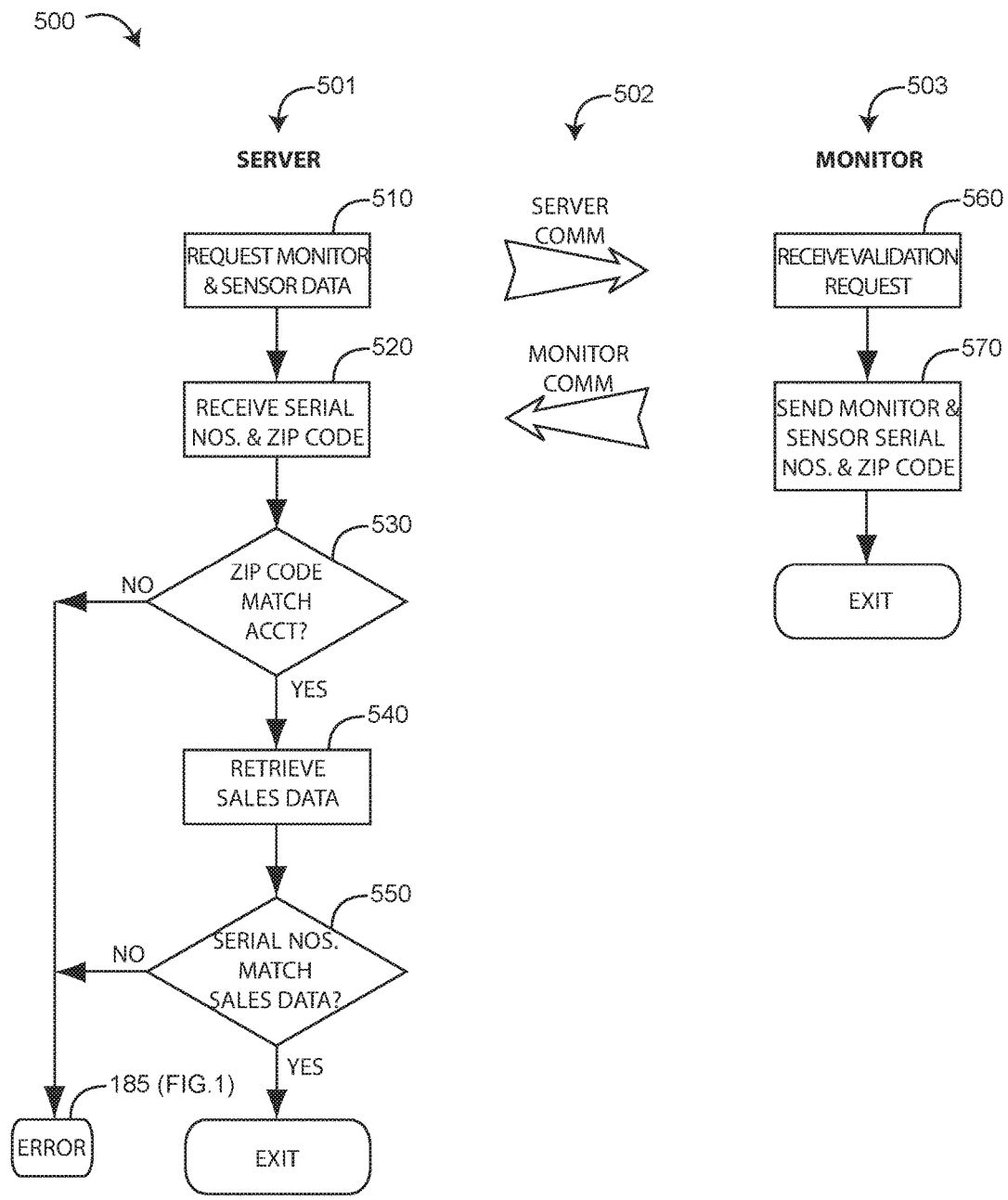
FIG. 5 is a flowchart of server and monitor account validation.

FIG. 5 illustrates monitor and user account validation 500. Validation is performed for direct from manufacturer sales or for sales through distributors. Several validation methods can be used. Monitor and a sensor serial numbers can be compared with sales order records or with tracing data from distributors. A zip code can be used in a manner similar to a credit card, i.e. to prevent a user from accessing a wrong account due to incorrect recording of serial numbers. An address can be used the same as a zip code, but is more secure. However, an address is prone to user error and free text input is difficult to validate. A web registration can be used for distribution sales or direct acute care sales.

As shown in FIG. 5, the server 501 requests monitor and sensor data 510. The monitor 503 receives the request 530 and complies 570. The server 501 receives the requested data 520, which is compared with server records 530-550 for a match. The server sends an error message 185 (FIG. 1) for a monitor to display 180 (FIG. 1), such as Contact Tech Support, if validation data does not match with sales records.

Figure 6:
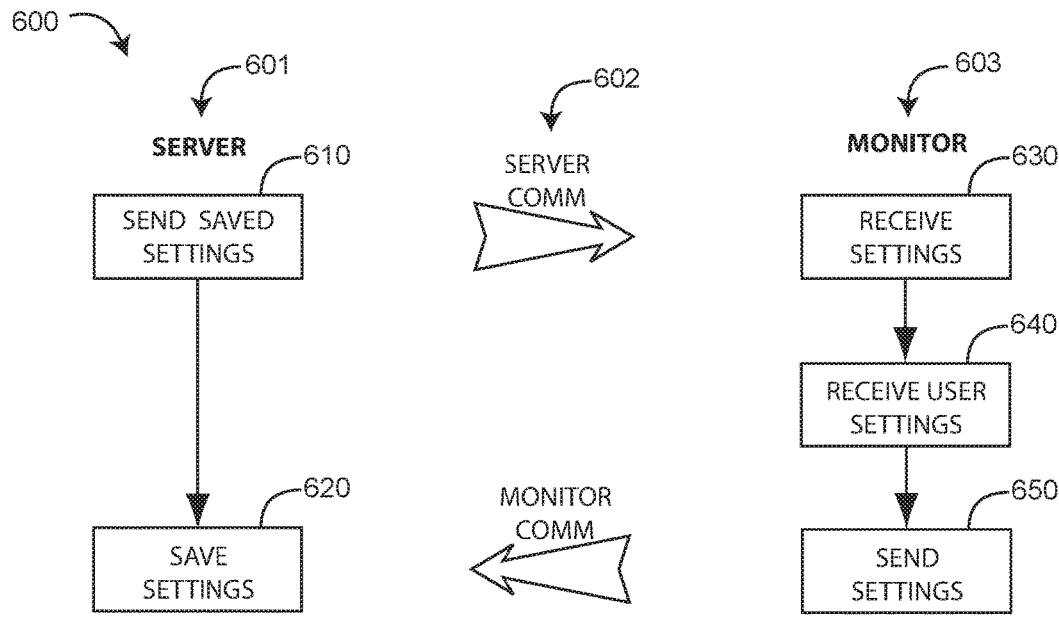
FIG. 6 is a flowchart of a server one-time monitor setup.

FIG. 6 illustrates a server 610 performing a monitor setup 600. The server 601 sends saved settings 610 to the monitor 630. The user can always change settings online 640. The monitor 650 sends these to the server to save 620. Any configuration parameters that the monitor needs to remember, such as the low credit threshold, are saved on the server side 601. The server 601 initially sends a set of commands/queries to the monitor to get configuration parameters (not shown). These parameters include: turn on/off auto-download; define threshold that initiates automatic download; and define number of credits to automatically download. The server may also perform an extra one-time validation, using, e.g., a zip code or the last 4 digits of an account number. If any errors occur on the monitor side, a local message is displayed and the connection is dropped. If any errors occur on server side, the server may choose to display an error message on the server side (via GUI commands) and drop the connection.

Figure 7:
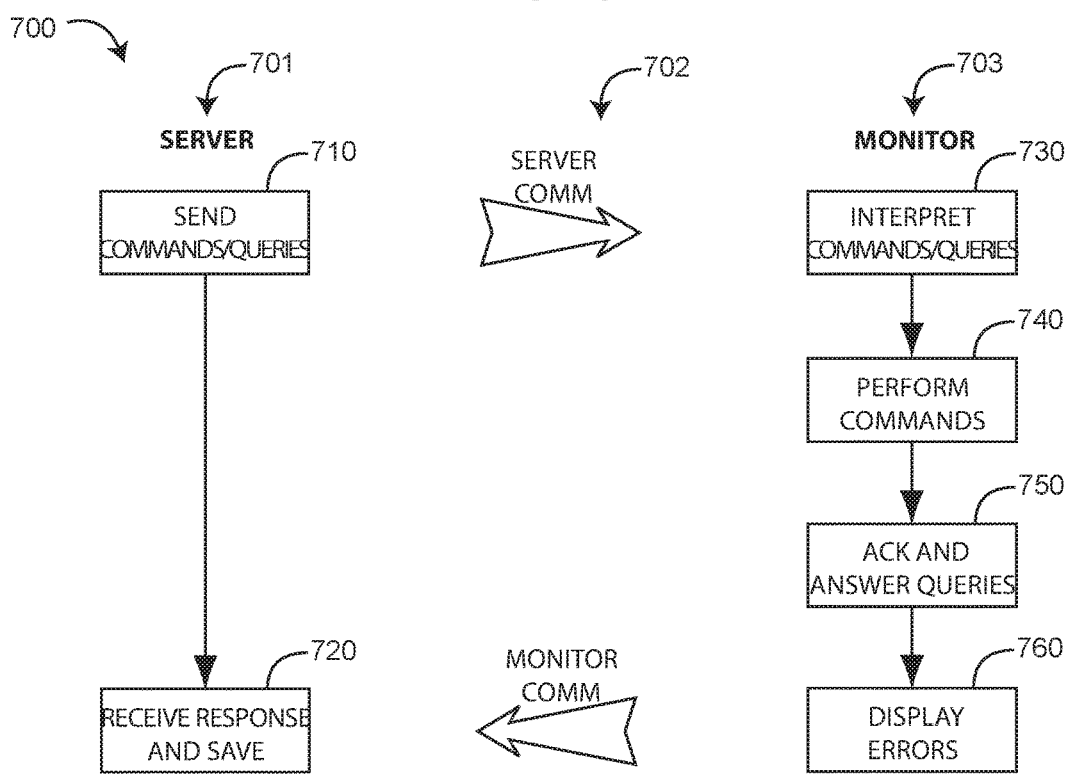
FIG. 7 is a flowchart of server command and monitor acknowledgement communications.

FIG. 7 illustrates server command and monitor acknowledgement communications 700. Once a connection is established, the server assumes the master role and the monitor assumes a slave role. The server 701 sends commands/queries 710, which the monitor 703 interprets 30. The monitor 703 performs the commands 740 and acknowledges/answers the queries 750. Any errors are displayed 760 on the monitor 703. The sensor 701 saves the monitor responses 720. In an embodiment, the server sends commands in a form of HTML-like NMEA data.

Figure 8A:
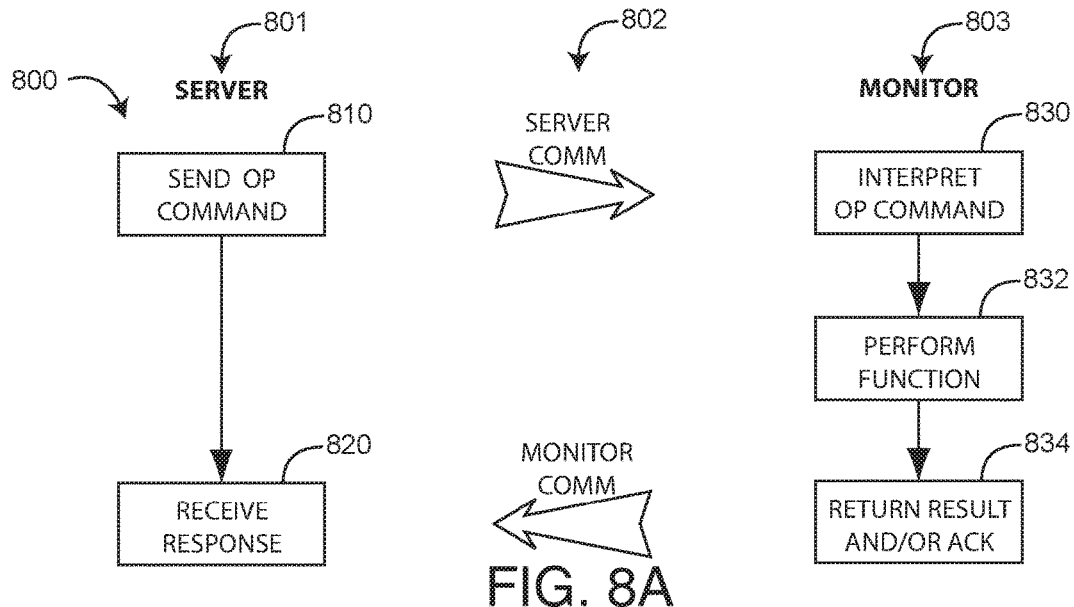
FIGS. 8A-C are flowcharts of server communications of and monitor responses to operational, GUI and hybrid commands.
Figure 8B:
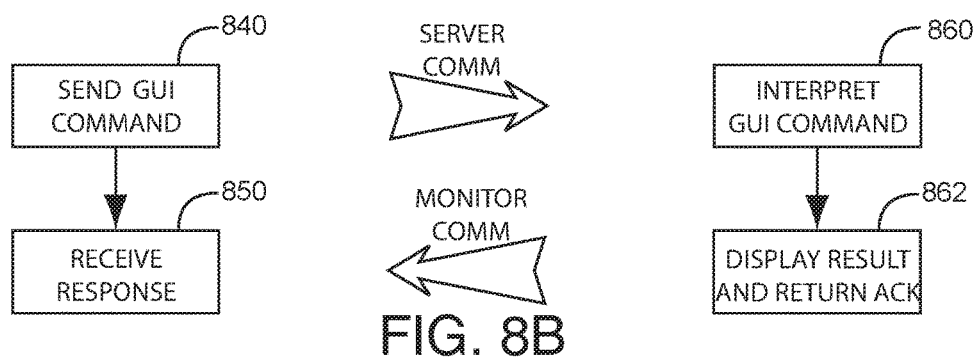
Figure 8C:
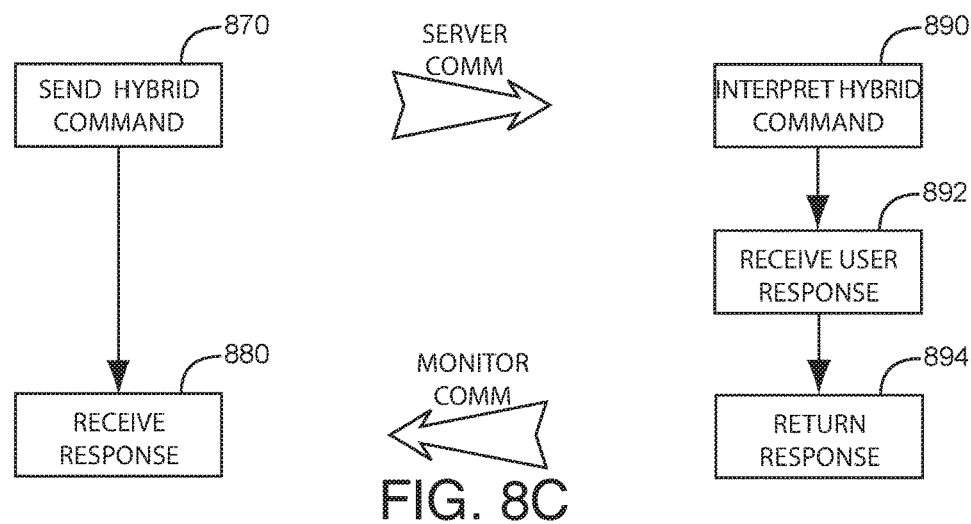

FIGS. 8A-C illustrate server commands and monitor responses to those commands. The server 801 may send three types of commands including an operational command 810, a GUI command 840 and a hybrid command 870. For example, an operational command 810 may be "get zip code," or "accept credit file and send back ACK." GUI commands 840 may be, for example, display message "online credit update in progress." A hybrid command 870 may be to display a GUI as well as expect a response from the monitor user. An example would be a command to display the message "want to turn on auto update?" and wait for a "yes" or "no" response.

As shown in FIGS. 8A-C, the monitor 803 response to an op command 830 is to perform a function 832 and return a result and/or ACK 834. The monitor 803 response to a GUI command 860 is to display a result and ACK 862. The monitor 803 response to a hybrid command 890 is to receive and return a user response 892, 894.

A physiological test credit method has been disclosed in detail in connection with various embodiments. These embodiments are disclosed by way of examples only and are not to limit the scope of the claims that follow. One of ordinary skill in art will appreciate many variations and modifications.

What is claimed is:

1. A physiological monitoring system configured to perform parameter spot-checks on a per test credit basis, the system comprising:
    a sensor configured to be placed at a measurement location of a patient and output signals indicative of the patient's physiological conditions, the sensor comprising a memory configured to store one or more test credits; and
    a patient monitor configured to be coupled to the sensor, the patient monitor comprising one or more signal processors configured to receive and process the signals received from the sensor to make a physiological measurement of the patient,
    wherein the patient monitor is enabled to make the physiological measurement by one of the one or more test credits stored in the memory of the sensor, a number of test credits stored in the memory decremented after each physiological measurement,
    wherein the patient monitor is configured to determine the number of stored test credits after each physiological measurement and initiate communication with a remote server in response to the number of stored test credits falling below a predetermined threshold so as to:
        securely connect to the server,
        receive additional test credits from the server,
        send an acknowledgement for receipt of the additional test credits to the server, and
        using a two-way handshake upon the server receiving the acknowledgement, update the number of test credits in the memory of the sensor when the server deducts the additional test credits from a user account and increments a test credit downloading index count.

2. The physiological monitoring system of claim 1, wherein the sensor comprises an optical sensor configured to transmit optical radiation at a plurality of wavelengths.

3. The physiological monitoring system of claim 1, wherein securely connecting the patient monitor to the server when remaining test credits fall below the predetermined threshold comprises the patient monitor exchanging challenges with the server.

4. The physiological monitoring system of claim 3, wherein the patient monitor exchanges challenges with the server by:
    receiving a server challenge code sent from the server;
    breaking the server challenge code; and
    sending a monitor challenge code to the server for the server to break the monitor challenge code.

5. The physiological monitoring system of claim 3, wherein securely connecting the patient monitor to the server when remaining test credits fall below the predetermined threshold further comprises the patient monitor sending to the server monitor and/or sensor data to be matched to sales and/or distributors data for patient monitor and user account validation.

6. The physiological monitoring system of claim 5, wherein the monitor and/or sensor data comprise device serial numbers, user zip code, and/or user address.

7. The physiological monitoring system of claim 5, wherein the monitor and user account validation is a one-time validation or a validation for every credit download.

8. The physiological monitoring system of claim 1, wherein the additional test credits comprises a user-predefined download quantum of test credits.

9. The physiological monitoring system of claim 8, wherein the patient monitor automatically adjusts the download quantum and/or the predetermined threshold according to a frequency of test credit usage.

10. The physiological monitoring system of claim 8, wherein the patient monitor automatically adjusts the download quantum and/or the predetermined threshold according to a frequency of test credit downloads.

11. A physiological test credit system configured to enable a physiological monitor to perform parameter spot-checks, the system comprising:
a patient monitor configured to be coupled to a physiological sensor, the monitor comprising one or more signal processors configured to, when enabled by a test credit stored in a memory of the physiological sensor, receive and process signals from the physiological sensor to make a physiological measurement of the patient, wherein the monitor decrements the number of test credits stored in the memory after each physiological measurement,
wherein the patient monitor is configured to initiate communication with a remote server in response to the number of stored test credits falling below a predetermined threshold after each physiological measurement, wherein upon securely connecting to the remote server, the patient monitor is configured to:
process server commands instructing the patient monitor to download additional test credits from the server,
download the additional test credits from the server and send an acknowledgement for receipt of the additional test credits to the server, and
upon the server receiving the acknowledgement, with a two-way handshake, update the number of test credits in the memory of the sensor when the server deducts the additional test credits from a user account and increments a test credit downloading index count.

12. The physiological monitoring system of claim 11, wherein the patient monitor is configured to make physiological measurements based on relative concentrations of blood constituents of the patient.

13. The physiological monitoring system of claim 11, wherein securely connecting the patient monitor to the server when remaining test credits fall below the predetermined threshold comprises the patient monitor exchanging challenges with the server.

14. The physiological monitoring system of claim 13, wherein the patient monitor exchanges challenges with the server by:
receiving a server challenge code sent from the server;
breaking the server challenge code; and
sending a monitor challenge code to the server for the server to break the monitor challenge code.

15. The physiological monitoring system of claim 13, wherein securely connecting the patient monitor to the server when remaining test credits fall below the predetermined threshold further comprises the patient monitor sending to the server monitor and/or sensor data to be matched to sales and/or distributors data for monitor and user account validation.

16. The physiological monitoring system of claim 15, wherein the monitor and/or sensor data comprise device serial numbers, user zip code, and/or user address.

17. The physiological monitoring system of claim 15, wherein the monitor and user account validation is a one-time validation or a validation for every credit download.

18. The physiological monitoring system of claim 11, wherein the additional test credits comprises a user-predefined download quantum of test credits.

19. The physiological monitoring system of claim 18, wherein the patient monitor automatically adjusts the download quantum and/or the predetermined threshold according to a frequency of test credit usage.

20. The physiological monitoring system of claim 18, wherein the patient monitor automatically adjusts the download quantum and/or the predetermined threshold according to a frequency of test credit downloads.

* * * * *